(12) United States Patent
Guimont et al.

(10) Patent No.: US 11,896,694 B2
(45) Date of Patent: *Feb. 13, 2024

(54) COMPOSITIONS FOR REMOVING NAIL POLISH

(71) Applicant: L'OREAL, Paris (FR)

(72) Inventors: Aline Aude Guimont, Westfield, NJ (US); Chunhua Li, Hillsborough, NJ (US); Hubert Tunchiao Lam, Berkeley Heights, NJ (US); Derek James Henry, Montclair, NJ (US)

(73) Assignee: L'OREAL, Paris (FR)

( * ) Notice: Subject to any disclaimer, the term of this patent is extended or adjusted under 35 U.S.C. 154(b) by 81 days.

This patent is subject to a terminal disclaimer.

(21) Appl. No.: 17/140,567

(22) Filed: Jan. 4, 2021

(65) Prior Publication Data

US 2021/0121377 A1    Apr. 29, 2021

Related U.S. Application Data

(63) Continuation of application No. 16/117,610, filed on Aug. 30, 2018, now Pat. No. 10,912,724.

(60) Provisional application No. 62/592,893, filed on Nov. 30, 2017.

(51) Int. Cl.
| | |
|---|---|
| *A61Q 3/04* | (2006.01) |
| *A61K 8/34* | (2006.01) |
| *A61K 8/49* | (2006.01) |
| *A61K 8/60* | (2006.01) |
| *A61K 8/81* | (2006.01) |

(52) U.S. Cl.
CPC ............... *A61K 8/345* (2013.01); *A61K 8/34* (2013.01); *A61K 8/4973* (2013.01); *A61K 8/60* (2013.01); *A61K 8/8152* (2013.01); *A61K 8/8158* (2013.01); *A61Q 3/04* (2013.01); *A61K 2800/28* (2013.01); *A61K 2800/30* (2013.01); *A61K 2800/31* (2013.01); *A61K 2800/48* (2013.01)

(58) Field of Classification Search
None
See application file for complete search history.

(56) References Cited

U.S. PATENT DOCUMENTS

| | | |
|---|---|---|
| 9,078,839 B1 | 7/2015 | Pascal, Sr. |
| 9,987,212 B2 | 6/2018 | MacNeill |
| 2004/0198620 A1 | 10/2004 | Johansson et al. |
| 2007/0004609 A1* | 1/2007 | Hloucha ................ C11D 3/222 |
| | | 524/157 |
| 2016/0354295 A1* | 12/2016 | MacNeill ............... C11D 3/201 |
| 2017/0246103 A1 | 8/2017 | Argembeaux et al. |

FOREIGN PATENT DOCUMENTS

| | | |
|---|---|---|
| CN | 101953769 A | 1/2011 |
| CN | 105078801 A | 11/2015 |
| CN | 107280990 A | 10/2017 |
| CN | 107280991 A | 10/2017 |
| CN | 107648125 A | 2/2018 |
| JP | 2017-052706 A | 3/2017 |
| JP | 2014139142 A2 | 7/2017 |
| KR | 10-2006-0099865 A | 9/2006 |
| TW | 201210624 A | 3/2012 |
| WO | 2016196114 A1 | 12/2016 |

OTHER PUBLICATIONS

Gentle Nail Remover, Mintel GNPD, p. 1-2, Published on Aug. 2012.
Tommy Girl Sugar Scrub, Mintel GNPD, p. 1-2, Published on Nov. 2001.
CN Office Action dated Apr. 15, 2023 from related CN Patent Application No. 201880079246.9 filed Nov. 26, 2018; 16 pages.

* cited by examiner

*Primary Examiner* — Susan T Tran
(74) *Attorney, Agent, or Firm* — WOMBLE BOND DICKINSON (US) LLP

(57) ABSTRACT

The invention relates to compositions for removing nail polish comprising at least at least about 10% by weight of at least one polyhydric alcohol compound, at least one low carbon alcohol, at least one high boiling point ester compound, at least one thickening agent, and at least one abrasive compound, as well as to methods of removing nail polish from nails using such compositions.

20 Claims, No Drawings

COMPOSITIONS FOR REMOVING NAIL POLISH

CROSS-REFERENCE TO RELATED APPLICATION

The present application is a continuation of and claims the benefit of priority to U.S. application Ser. No. 16/117,610, filed Aug. 30, 2018, which claims the benefit of U.S. Provisional Application No. 62/592,893, filed Nov. 30, 2017.

FIELD OF THE INVENTION

The present invention relates to compositions and methods for removing nail polish.

DISCUSSION OF THE BACKGROUND

Nail polish compositions are typically designed to provide long-lasting color to nails. Because of the materials used in nail polish compositions to obtain the desired properties, it has proven difficult to remove such nail polish compositions from nails without adversely affecting the nails and/or staining cuticles of the nails.

In particular, the inventors have recognized the need to provide efficacious nail polish removal using compositions that are substantially free of harsh solvents such as acetone.

SUMMARY OF THE INVENTION

The present invention relates to compositions for removing nail polish including at least about 10% by weight of at least one polyhydric alcohol compound, at least one low carbon alcohol, at least one high boiling point ester compound, at least one thickening agent, and at least one abrasive compound. In certain embodiments, the compositions for removing nail polish are substantially free of water and/or acetone. In certain other embodiments, the at least one abrasive compounds includes a soft abrasive and a moderately hard abrasive. In certain other embodiments, the composition the soft abrasive is a sugar.

In another aspect, the present invention relates to methods of removing nail polish from nails comprising applying a composition for removing nail polish described above to nails onto which nail polish has been previously applied and removing the nail polish from the nails. The composition includes at least about 10% by weight of at least one polyhydric alcohol compound, at least one low carbon alcohol, at least one high boiling point ester compound, at least one thickening agent, and at least one abrasive compound.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations. All percentages listed are by weight unless otherwise noted.

Other than in the operating examples, or where otherwise indicated, all numbers expressing quantities of ingredients and/or reaction conditions are to be understood as being modified in all instances by the term "about," meaning within 10% to 15% of the indicated number.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Nail" as used herein includes fingernails as well as toenails.

The compositions, coats and methods of the present invention can comprise, consist of, or consist essentially of the essential elements and limitations of the invention described herein, as well as any additional or optional ingredients, components, or limitations described herein or otherwise useful.

For purposes of the compositions and methods of the present invention where the invention "consists essentially of" the identified ingredients and/or process steps, the two "basic and novel properties" of such compositions and/or methods are "removing nail polish from nails" and "minimizing staining of cuticles."

Numerical ranges are inclusive of endpoints and meant to include all combinations and sub-combinations. For example, from about 5%, 10% or 15% to about 20%, 50% or 60% means about 5% to about 20%, about 5% to about 50%, about 5% to about 60%, about 10% to about 20%, about 10% to about 50%, about 10% to about 60%, about 15% to about 20%, about 15% to about 50%, or about 15% to about 60%.

Compositions for Removing Nail Polish

In accordance with the present invention, compositions for removing nail polish comprising at least about 10% by weight of at least one polyhydric alcohol compound, at least one low carbon alcohol, at least one high boiling point ester compound, at least one thickening agent, and at least one abrasive compound are provided.

Polyhydric Alcohol Compound

In accordance with the present invention, compositions for removing nail polish comprising at least one polyhydric alcohol compound are provided. The polyhydric alcohol compound may be selected from the group consisting of glycerin, glycols, polyglycerin, esters of polyhydric alcohols, and mixtures thereof.

Suitable glycols include those that are liquid at room temperature. The glycol may contain from 2 to 12 carbon atoms, such as from 2 to 10 carbon atoms such as, for example, glycerin, propylene glycol, butylene glycol, propane diol, hexylene glycol, polyglycerin, dipropylene glycol and diethylene glycol. In certain other embodiments the polyhydric alcohol compound includes glycerin, propylene glycol, butylene glycol, propane diol, hexylene glycol, polyglycerin, and combinations thereof. In certain other embodiments the polyhydric alcohol is glycerin.

Suitable esters of polyhydric alcohol include liquid esters of saturated or unsaturated, linear or branched C1-C26 polyhydric alcohols. The total number of carbon atoms of the esters may be greater than or equal to 8, such as greater than or equal to 10, such as greater than or equal to 12 and such as less than 50, including all ranges and subranges therebetween such as 8 to 50, 10 to 40, 12 to 30, 8 to 25, 10 to 50, etc. Specific examples of suitable esters of polyhydric alcohol include, but are not limited to, esters of dihydroxy, trihydroxy, tetrahydroxy or pentahydroxy alcohols. The ester of polyhydric alcohol may be a glyceryl ester such as, for example, glyceryl triglycolate, glyceryl tricitrate, glyceryl trilactate, glyceryl trilactate, glyceryl tributanoate, glyceryl triheptanoate, glyceryl trioctanoate, etc.

According to certain embodiments, the at least one polyhydric alcohol compound is present in the compositions of the present invention in an amount greater than about 15% by weight, such as greater than about 20% by weight, such as greater than about 50% by weight, including all ranges and subranges therebetween such as, for example, from 5% to 50%, from 10% to 50%, from 15% to 50%, from 20% to 50%, from 10% to 40%, from 15% to 30%, etc., with all weights being based on the weight of the composition.

Low Carbon Alcohol

In accordance with the present invention, compositions for removing nail polish comprising at least one low carbon alcohol are provided.

"Low carbon alcohol" means an alcohol containing from 1 to 8 carbon atoms. The low carbon alcohol may contain from 2 to 6 carbon atoms, such as from 2 to 5 carbon atoms. Examples of low carbon alcohols include, but are not limited to, ethanol, propanol, butanol, pentanol, isopropanol, isobutanol, and isopentanol.

The at least one low carbon alcohol may be present in the compositions of the present invention in an amount greater than 5% by weight, such as greater than 10% by weight, such as greater than 15% by weight, such as greater than 20% by weight and such as less than 50% by weight, including all ranges and subranges therebetween such as, for example, from 5% to 50%, from 10% to 50%, from 15% to 50%, from 20% to 50%, from 10% to 40%, from 15% to 30%, etc., with all weights being based on the weight of the composition.

High Boiling Point Ester Compound

In accordance with the present invention, compositions for removing nail polish comprising at least one high boiling point ester compound are provided. "High boiling point ester compound" means an ester compound having a boiling point greater than 90° C. The high boiling point ester compound may have a boiling point greater than 125° C., such as greater than 175° C., and such as greater than 200° C.

Suitable high boiling point ester compounds include, but are not limited to, esters of C4-C22 dicarboxylic or tricarboxylic acids and of C1-C22 alcohols, such as C1-C8 alcohols, and such as C1-C3 alcohols. Notable high boiling point ester compounds include carbonate esters, adipates, sebacates and succinates. Specific examples of high boiling point ester compounds include, but are not limited to, alkylene carbonates such as propylene carbonate, dimethyl succinate, diethyl succinate, dimethyl glutarate, diethyl glutarate, dimethyl sebacate, diethyl sebacate, diisopropyl sebacate, bis(2-ethylhexyl) sebacate, dimethyl adipate, diisopropyl adipate, di-n-propyl adipate, dioctyl adipate, bis(2-ethylhexyl) adipate, diisostearyl adipate, ethyl maleate, bis (2-ethylhexyl) maleate, triisopropyl citrate, triisocetyl citrate, triisostearyl citrate, trioctyldodecyl citrate and trioleyl citrate.

The at least one high boiling point ester compound may be present in the compositions of the present invention in an amount greater than 10% by weight, such as greater than 15% by weight, such as greater than 20% by weight and such as less than 50% by weight, including all ranges and subranges therebetween such as, for example, from 10% to 50%, from 15% to 50%, from 20% to 50%, from 10% to 40%, from 15% to 30%, etc., with all weights being based on the weight of the composition.

Thickening Agent

In accordance with the present invention, compositions for removing nail polish comprising at least one thickening agent are provided. Non-limiting examples of thickening agents that may be used according to various embodiments of the present invention include those conventionally used in cosmetics, such as polymers of natural origin and synthetic polymers. For example, nonionic, anionic, cationic, amphiphilic, and amphoteric polymers, and other known rheology modifiers, such as cellulose-based thickeners, may be used.

According to certain embodiments, the thickening agent is a cellulose-based thickener. Suitable cellulose-based compounds include, but are not limited to, cellulose polymers, such as, for example, hydroxyethylcellulose, hydroxypropylcellulose, methylcellulose, and ethylhydroxyethylcellulose. Certain notable cellulose derivatives include hydroxyl-modified cellulose polymers such as Hydroxyethylcellulose, e.g., those having a molecular weight over 500,000 daltons such as NATROSOL 250 HHR and Hydroxypropyl cellulose, e.g., KLUCEL MF—both available from Ashland of Covington, Kentucky.

According to other embodiments, the thickening agent is a polysaccharide.

In general, polysaccharides may be divided into several categories. Polysaccharides that are suitable for use in the invention may be homopolysaccharides such as fructans, glucans, galactans and mannans or heteropolysaccharides such as hemicellulose.

Suitable polysaccharides may be linear polysaccharides such as pullulan or branched polysaccharides such as gum arabic and amylopectin, or mixed polysaccharides such as starch.

Suitable polysaccharides may be starchy polysaccharides. Starchy polysaccharides include, but are not limited to, native starches, modified starches and particulate starches. The native starches that may be used in the present invention are more particularly macromolecules in the form of polymers consisting of elemental units which are anhydroglucose (dextrose) units, linked via a (I,4) bonds, of chemical formula $(C_6H_{10}O_5)_n$. The number of these units and their assembly make it possible to distinguish amylose, which is a molecule formed from about 600 to 1000 linearly linked glucose molecules, and amylopectin, which is a polymer that is branched every 25 glucose residues approximately ((I,6) bond). The total chain may contain between 10 000 and 100 000 glucose residues.

The botanical origin of starch may be cereals or tubers. Thus, the starches are chosen, for example, from corn starch, rice starch, cassava starch, tapioca starch, barley starch, potato starch, wheat starch, sorghum starch and pea starch.

According to other embodiments, the thickening agent is an acrylic thickening agent (acrylic thickener) or an acrylamide thickening agent (acrylamide thickener).

"Acrylic thickening agent" or "acrylic thickener" as used herein refers to polymers based upon one or more (meth) acrylic acid (and corresponding (meth)acrylate) monomers or similar monomers.

"Acrylamide thickening agent" or "acrylamide thickener" as used herein refers to polymers based upon one or more acrylamide monomers or similar monomers.

According to other embodiments, the thickening agent comprises at least one monomer performing a weak acid function such as, for example, acrylic acid, methacrylic acid, itaconic acid, crotonic acid, maleic acid and/or fumaric acid.

According to other embodiments, the thickening agent comprises at least one monomer performing a strong acid function such as, for example, monomers having a function of the sulfonic acid type or phosphonic acid type, such as 2-acrylamido-2-methylpropane sulfonic acid (AMPS).

According to other embodiments, the thickening agent may be crosslinked (or branched). Suitable examples of acceptable crosslinking agents include, but are not limited to, methylene bisacrylamide (MBA), ethylene glycol diacrylate, polyethylene glycol dimethacrylate, diacrylamide, cyanomethacrylate, vinyloxyethacrylate or methacrylate, formaldehyde, glyoxal, and compositions of the glycidylether type such as ethyleneglycol diglycidylether, or epoxides.

Suitable acrylic thickeners are disclosed in U.S. patent application publication nos. 2004/0028637 and 2008/0196174, the entire contents of both of which are incorporated herein by reference.

Specific non-limiting examples of suitable thickening agents include homopolymers or copolymers of acrylic or methacrylic acids or the salts thereof and the esters thereof, such as the products sold under the names VERSICOL F® or VERSICOL K® by Allied Colloid, ULTRAHOLD 8® by Ciba-Geigy, polyacrylates and polymethacrylates such as the products sold under the names LUBRAJEL and NORGEL by Guardian, or under the name HISPAJEL by Hispano Chimica, polyacrylic acids of SYNTHALEN K type, polyacrylamides, copolymers of acrylic acid and of acrylamide sold in the form of the sodium salt thereof, such as under the names RETEN® by Hercules, the sodium polymethacrylate such as sold under the name DARVAN 7® by Vanderbilt, and the sodium salts of polyhydroxycarboxylic acids such as sold under the name HYDAGEN F® by Henkel, optionally crosslinked and/or neutralized 2-acrylamido-2-methylpropanesulphonic acid polymers and copolymers, for instance poly(2-acrylamido-2-methylpropanesulphonic acid) such as sold by Clariant under the name HOSTACERIN AMPS (INCI name: ammonium polyacryldimethyltauramide), crosslinked anionic copolymers of acrylamide and of AMPS, e.g. in the form of a water-in-oil emulsion, such as those sold under the name SEPIGEL® 305 (CTFA name: Polyacrylamide/C13-14 Isoparaffin/Laureth-7) and under the name SIMULGEL® 600 (INCI name: Acrylamide/Sodium acryloyldimethyltaurate copolymer/Isohexa-decane/Polysorbate 80) by SEPPIC, polyacrylic acid/alkyl acrylate copolymers of PEMULEN type, sodium acrylate/sodium acryloyldimethyl taurate such as that sold under the INCI name Sodium Acrylate/Sodium Acryloyldimethyl Taurate Copolymer & Hydrogenated Polydecene & Sorbitan Laurate & Trideceth-6 which is marketed by Lonza, Allendale, N.J., USA under the tradename ViscUp® EZ. Certain especially notable acrylic thickeners are selected from the group of: Acrylamide/Sodium Acryloyldimethyl Taurate Copolymer such as those provided in Isohexadecane & Polysorbate 80 as SIMULGEL 600 and SIMULGEL 800; Polyacrylamide provided with C13-14 isoparaffin and laureth-7 available as SEPIGEL 305; and Polyacrylate Crosspolymer-6 available as SEPIMAX ZEN. SIMULGEL, SEPIGEL, and SEP IMAX products are available from Seppic Inc. of Paris, France. In certain embodiments, the thickening agent is selected from polyacrylamides and water soluble cellulose polymers (such as hydroxypropylmethylcellulose, ethylcellulose, and/or hydroxypropylcellulose), and combinations thereof.

According to other embodiments, the thickening agent is an organoclay (hydrophobically treated clay) or a hydrophilic clay. The term "hydrophilic clay" means a clay that is capable of swelling in water; this clay is activated in water and forms after hydration a colloidal dispersion. These clays are products that are already well known per se, which are described, for example, in the book "Mineralogie des argiles", S. Caillere, S. Henin, M. Rautureau, $2^{nd}$ edition 1982, Masson, the teaching of which is included herein by way of reference. Clays are silicates containing a cation that may be chosen from calcium, magnesium, aluminium, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin. Hydrophilic clays that may be mentioned include smectite products such as saponites, hectorites, montmorillonites, bentonites and beidellite.

The term "lipophilic clay" (or hydrophobically treated clay) means a clay that is capable of swelling in a lipophilic medium; this clay swells or becomes "activated" in a hydrophobic solvent and thus forms a colloidal dispersion. Examples of lipophilic clays that may be mentioned include modified clays such as modified hectorite, such as those modified with a $C_{10}$ to $C_{22}$ fatty-acid ammonium chloride. Examples include hectorite modified with distearyldimethylammonium chloride (INCI name: disteardimonium hectorite).

In particular, among the thickening agents that may be used, mention may be made of silica particles. Suitable silicas include, but are not limited to, hydrophobic synthetic amorphous silicas, pyrogenic or fumed silica optionally with hydrophobic surface treatment with particle size less than 10 microns, such as less than 500 nm, such as less than 100 nm, such as from 5 nm to 30 nm, including all ranges and subranges therebetween.

The at least one thickening agent may be present in the compositions of the present invention in an amount greater than 0.05% by weight, such as greater than 0.1% by weight, such as greater than 0.5% by weight, such as greater than 1% by weight and such as less than 15% by weight, including all ranges and subranges therebetween such as, for example, from 0.1% to 15%, such as from 0.1% to 10%, such as from 0.5% to 10%, such as from 0.75% to 7.5%, such as from 1% to 5%, etc., with all weights being based on the weight of the composition.

Abrasive Compound

In accordance with the present invention, compositions for removing nail polish comprising at least one abrasive compound (abrasive system) are provided. An "abrasive compound" is a compound capable of providing abrasion or mechanical exfoliation and in accordance with the present invention may have one or more of the following characteristics:

(1) Surface roughness: particles with irregular edges provide for abrasion; (2) shape: the particles of the abrasive compound may have a non-angular shape such as a disc, oval or sphere; (3) average particle size: such as, in the context of abrasive compounds from mineral origins, shells, seeds, micronized fruit kernel powders, and the like. The particles of the abrasive may have a particle size of 1000 microns (µm) or less, such as 500 µm or less, such as 300 µm or less, such as 150 µm or less, such as 75 µm or less, such as, 50 µm or less such as 30 µm or less; and (4) Hardness: the abrasive particles may be soft so as to provide for mild abrasion. According to certain embodiments, the abrasive of the present invention has at least two of the above-mentioned properties, such as at least three of the above-mentioned properties, such as all four of the above-mentioned properties. For example—the abrasive compound may be a large spherical material and not hard; or very small, hard, and having an irregular shape.

The inventors have found that it is desirable, in order to provide both fast nail polish removal without compromising the skin, according to certain embodiments of the invention, that the at least one abrasive compound includes both a soft abrasive and a moderately hard abrasive. The moderately hard abrasive may be characterized as having a Mohs hardness between 3-8 (inclusive of endpoints of 3 and 8), and/or a Shore D of 40-60. in case the particle is a wax, polymer or any kind of abrasive particles). According to certain embodiments the moderately hard abrasive has a Mohs hardness between 4-8, such as between 4-6.5.

The abrasive particles including the moderately hard abrasive may be selected from, for example, perlite, pumice, zeolites, hydrated silica, calcium carbonate, dicalcium phosphate dihydrate, calcium pyrophosphate, alumina, sodium bicarbonate, polylactic acid, as well as synthetic polymeric materials such as polyethylene, polypropylene, polyethylene terephthalate, polymethyl methacrylate or nylon. In certain embodiments the moderately hard abrasive includes perlite, such as a cosmetic grade perlite available from Imerys under the name ImerCare® 270P-Scrub.

The soft abrasive may be selected from a water-soluble abrasive such as, for example, sugar; ground fruit kernel or shell powders such as apricot kernel, coconut husk; or spherical waxes (for example, carnauba jojoba); argan shell powder, and the like.

The inventors have further found that it is desirable, in order to provide both fast nail polish removal without compromising the skin, according to certain embodiments of the invention, that the soft abrasive may be present in the composition in a weight concentration of soft abrasive that is from about 5 to about 50 times as great as a weight concentration of the moderately hard abrasive.

Because of the way in which abrasive compounds are produced or manufactured, it is to be understood that not all particles of abrasive compounds used in accordance with the present invention have the properties discussed above. That is, it is to be understood that the abrasive compound will contain particles having a distribution of smoothnesses, shapes, sizes and hardnesses. A majority of the particles of the abrasive compound or blends thereof used in accordance with the present invention may have the smoothness, shape, size and/or hardness characteristics discussed above, such as greater than 60% of the particles, such as greater than 70% of the particles, such as greater than 80% of the particles and such as greater than 90% of the particles.

Such as, the total amount of the at least one abrasive compound is present in the compositions of the present invention in an amount greater than 0.5% by weight, such as greater than 1% by weight, such as greater than 2.5% by weight, such as greater than 5% by weight and such as less than 40% by weight, including all ranges and subranges therebetween such as, for example, from 0.5% to 40%, such as from 1% to 30%, such as from 2.5% to 25%, such as from 5% to 20%, etc., with all weights being based on the weight of the composition. According to certain embodiments, the at least one soft abrasive is present in a concentration range as described above in this paragraph. According to certain other embodiments, the moderately hard abrasive is present in a concentration from about 0.1% to about 5%, such as from about 0.1% or 0.25% or 0.5% to about 1% or 2% or 5%.

According to other embodiments of the present invention, the compositions for removing nail polish are "essentially free" of acetone, water or both, "substantially free" of acetone, water, or both, or "free" of acetone, water or both. "Essentially free" means that the composition contains less than about 3% of the identified ingredient. "Substantially free" means that the composition contains less than about 2% of the identified ingredient. "Free" means that the composition contains less than 1% of the identified ingredient. A composition containing "no water" or "no acetone" contains about 0% of the identified ingredient. In certain other embodiments of the invention, the concentration of water may be less than about 20% by weight, such as less than about 15% by weight, less than about 10% by weight in the composition.

The inventors have also surprisingly found that maintaining low levels as opposed to higher levels of oil in the composition can improve the ability to maintain sufficient viscosity and suspending power. Accordingly, in certain embodiments of the invention the compositions are have less than about 5% by weight of oils and may, in certain embodiments be essentially free, substantially free, or free of oils. As used herein, by "oils," it is meant compounds having a melting point of less than about 30° C. and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy) sulfonyl moieties. In certain embodiments, the oil does not include hydroxyl moieties.

Suitable examples of compounds of oils include vegetable oils (glyceryl esters of fatty acids, monoglycerides, diglycerides, triglycerides) and fatty esters. Specific non-limiting examples include, without limitation, esters such as isopropyl palmitate, isopropyl myristate, isononyl isonanoate $C_{12}$-$C_{15}$alkyl benzoates, caprylic/capric triglycerides, ethylhexyl hydroxystearate, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxyxcinnamate, among others.

According to certain other embodiments of the invention, compositions of the present invention are substantially free of surfactants and/or emulsifiers. One skilled in the art will recognize that such materials are used to perform one or more functions such as reduce surface tension, provide foaming, or emulsify oils present in the composition.

According to other embodiments of the present invention, the compositions of the present invention are for removing nail polish from nails. However, it is to be understood that the compositions of the present invention can also be used to clean keratinous materials such as skin and hair, and in particular can be used to clean hands.

Auxiliaries/Additives

The compositions discussed above may additionally comprise an additive or auxiliary commonly used in cosmetic compositions and known to a person skilled in the art as being capable of being incorporated into a nail polish remover composition. Such additives or auxiliaries may be chosen from solvents, preservatives, fragrances, oils, waxes, surfactants, antioxidants, agents for combating free radicals, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and the like, and their mixtures.

A person skilled in the art will take care to select the optional additional additives and/or the amount thereof such that the advantageous properties of the compositions according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 40% (such as from 0.01% to 30%) relative to the total weight of the composition.

Needless to say, the compositions of the invention should be cosmetically or dermatologically acceptable, i.e., they should contain a non-toxic physiologically acceptable. The compositions may be in any galenic form normally employed in the cosmetic and dermatological fields which is suitable for topical administration onto nails.

The compositions according to the invention can be manufactured by known processes used generally in the cosmetics or dermatological field.

According to other embodiments, methods of removing nail polish from nails including applying a composition for removing nail polish described above to nails onto which nail polish has been previously applied and removing the nail polish from the nails are provided.

According to certain other embodiments, methods of removing nail polish from nails and moisturizing hands include the steps of applying a composition for removing nail polish described above to the hands as well as to the nails onto which nail polish has been previously applied; and removing the nail polish from the nails. The composition may also be rinsed from the hands and nails such as with water. In certain embodiments, compositions of the present invention may be advantageously used without an absorbent pad (otherwise commonly used to remove nail polish from the nails).

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example I

Exemplified Compositions

TABLE 1

| Ingredient | Amount |
| --- | --- |
| Propylene Carbonate | 20-40% |
| Ethanol | 20-40% |
| Glycerin | 15-30% |
| Sugar Particles | 15-20% |
| Moderately abrasive particles | 1-3% |
| Acrylic or Acrylamide Thickener | 1-5% |
| Misc (Oil, Filler, Colorant, Water) | 1-10% |

Example I

Stain Prevention Testing #1 (In-Vivo)

An experiment was conducted to assess cuticle staining from nail polish that was removed with compositions including ethanol, propylene carbonate, glycerin, an acrylic thickener, as well having sucrose, perlite and an organic shell powder suspended therein. The compositions were free of acetone and substantially free of water. Two coats of nail polish (Essie Russian Roulette, L'Oreal SA, Paris, France) was applied to the finger nails of two consumers. A comparative example (Comparative Example 1) with 4.9% glycerin, a ratio of glycerin to propylene carbonate of about 1:8, and 20% of abrasive was compared with a similar inventive example having a higher amount of glycerin (about 28%) and a ratio of glycerin to propylene carbonate of about 1.15:1 (Inventive Example 1). It was also compared to another inventive example (Inventive Example 2) also the same amount of glycerin as Inventive Example 1, but having only 15% abrasive. For each of the compositions to be tested, nail polish on two separate individuals' hands were evaluated. The inventive examples showed no cuticle staining after removal, whereas the Comparative Example 1 showed significant staining of the cuticles. The results indicate that for compositions including ethanol, propylene carbonate and glycerin, levels of glycerin above 10% show surprisingly beneficial resistance to cuticle staining, in-vivo.

Example II

Stain Prevention Testing #2 (In-Vitro)

Neoprene was chosen as a proxy for keratin/human cuticle material. Neoprene substrates were obtained from cuts of NeoTouch™ Neoprene gloves (5 mil thick, powder free). The green colored gloves were cut open and the surrounding of the glove surface was taped with double sided tape to a black drawdown card. NeoTouch™ gloves are available from Ansell of Iselin, NJ. Five test compositions were prepared with varying amounts of glycerin. The test compositions included ethanol, propylene carbonate, glycerin, an acrylic thickener, as well having sucrose suspended therein. The compositions were free of acetone and substantially free of water. To each of the test compositions, enough nail polish (Essie Russian Roulette, L'Oreal SA, Paris, France) was added to create a 3.3% solution of nail polish therein. A small drop of the test composition having the nail polish dissolved therein was applied to the neoprene substrate. After five minutes the drop was removed with a cotton pad saturated in deionized water. The remaining stain was visually assessed for intensity and with a colorimeter (Datacolor 600™ from Datacolor Spectrum of Lawrenceville, NJ). The amount of glycerin as well as the corresponding test results are shown in Table 2, below.

TABLE 2

| Reference | Glycerin Concentration | Staining results |
|---|---|---|
| Comparative Example 2 | 5% | Continuous staining of surface, slightly darker at rim. |
| Inventive Example 3 | 10% | Slight staining at rim. Very slight staining toward edges. |
| Inventive Example 4 | 15% | Slight staining at rim. No staining elsewhere. |
| Inventive Example 5 | 20% | Slight staining at rim. No staining elsewhere. |
| Inventive Example 6 | 23% | Slight staining at rim. No staining elsewhere. |

The results above indicate when tested in vitro, we also see that for compositions including ethanol, propylene carbonate and glycerin, glycerin concentrations above 10% again surprisingly show beneficial resistance to cuticle staining.

Example III

Rheology Testing

A mixture was prepared by combining 30% glycerin, 38% propylene carbonate, and 32% ethanol. To this mixture either castor oil or isopropyl palmitate was added to the composition to provide five test compositions having the concentrations of oil as shown in Table 3 below. Furthermore, sufficient SEPPIGEL 305 was added to the samples to bring the concentration of SEPPIGEL 305 to 3.5 percent by weight. The samples were mixed using a high speed mixer for at least two minutes at about 2750 rpm. Using a magnetic bearing rheometer, the Discovery HR-3 rheometer from TA Instruments of New Castle, Delaware, available from TA Instruments of New Castle, Delaware], a rheology study was completed for each test composition. Yield stress and (low shear rate) viscosity measured at @0.1 s$^{-1}$ (Pa·s) were recorded, as per Table 3, below.

TABLE 3

Effect of Oil on Rheological Properties

| Reference | Oil | Concentration | Yield Stress (Pa) | Viscosity @0.1 s$^{-1}$ (Pa · s) |
|---|---|---|---|---|
| Inventive Example 7 | — | 0% | 105 | 324 |
| Inventive Example 8 | Castor oil | 1% | 123 | 329 |
| Inventive Example 9 | Castor oil | 5% | 57 | 252 |
| Inventive Example 10 | Isopropyl palmitate | 5% | 93 | 300 |
| Comparative Example 3 | Castor oil | 10% | 22 | 162 |

It can be seen from the above results that the presence of oil reduces the yield stress and low shear rate viscosity both decrease. With levels of oil exceeding 1% yield stress drops below 100 Pa, and with levels of oil exceeding 5%, yield stress drops below 50 Pa. Yield stress below 100 Pa can gradually start to compromise the ability to suspend abrasives therein. Yield stress below 50 Pa is low enough to create significant risk for the abrasive to remain suspended over time. Furthermore, such low yield stresses make the composition messier to use for nail polish removal.

Example IV

Hydration Testing

A test composition (Inventive Example 11) was prepared with ethanol, propylene carbonate, glycerin, an acrylic thickener, as well having sucrose, perlite, and argan shell powder suspended therein. The compositions were free of acetone and substantially free of water. The ability of the composition to promote hydration was evaluated with a corneometer (CM 825 from Courage and Khazaka Electronic GmbH of Cologne, Germany). The test composition was applied to human abdominal ex-vivo stratum corneum samples (3 replicates) and allowed to remain in contact for five minutes, then rinsed with water, allowed to dry overnight, and compared versus a baseline (untreated skin) and control (water treatment only). The average degree of hydration (expressed in corneometer units) was 24 (std. dev 1.9) for the control before treatment (baseline) and remained 24 after treatment (std. dev 1.1). For the test composition, the hydration was 24 (std. dev 2.2) prior to treatment and rose to 32 after treatment (std. dev 1.2). The improvement in hydration was statistically significant. This indicates that the test composition, despite having abrasive and other ingredients effective at removing durable nail polish, was surprisingly able to maintain and improve the hydration status of the skin.

What is claimed is:

1. A composition for removing nail polish comprising at least about 10% by weight of at least one polyhydric alcohol compound, at least 10% by weight of at least one C2-C5 alcohol, at least 15% by weight of at least one high boiling point ester compound, at least one thickening agent, and at least 5% by weight of at least one water-soluble abrasive having a hardness which provides mechanical exfoliation during said removing of nail polish, wherein the composition comprises less than about 5% by weight of oil, all weights being based on the weight of the composition.

2. The composition of claim 1 comprising at least about 15% by weight of the at least one polyhydric alcohol compound.

3. The composition of claim 1 comprising at least about 20% by weight of the at least one polyhydric alcohol compound.

4. The composition of claim 1 wherein the composition further comprises at least one moderately hard abrasive.

5. The composition of claim 1 wherein the water-soluble abrasive is a sugar.

6. The composition of claim 4 wherein the water-soluble abrasive is present in a weight concentration of water-soluble abrasive that is from about 5 to about 50 times as great as a weight concentration of the moderately hard abrasive.

7. The composition of claim 1, wherein the composition has a yield stress of at least about 100 Pascals.

8. The composition of claim 1, wherein the composition comprises from 10% to 50% by weight of at least one polyhydric alcohol compound, from 10% to 50% by weight of at least one C2-C5 alcohol, from 15% to 50% by weight of at least one high boiling point ester compound, and from 5% to 20% by weight of at least one water-soluble abrasive, all weights being based on the weight of the composition.

9. The composition of claim 1, wherein the composition is substantially free of acetone.

10. The composition of claim 1, wherein the composition is substantially free of water.

11. The composition of claim 1, wherein the composition is free of acetone.

12. The composition of claim 1, wherein the at least one polyhydric alcohol compound is selected from the group consisting of glycerin, propylene glycol, butylene glycol, propane diol, hexylene glycol, polyglycerin, and combinations thereof.

13. The composition of claim 1, wherein the at least one C2-C5 alcohol is ethanol.

14. The composition of claim 1, wherein the at least one high boiling point ester compound is propylene carbonate.

15. The composition of claim 1, wherein the at least one thickening agent is selected from the group consisting of an acrylic thickener, an acrylamide thickener, and mixtures thereof.

16. A method of removing nail polish from nails and moisturizing hands comprising:
applying a composition of claim 1 to the hands and to nails onto which nail polish has been previously applied; and
removing the nail polish from the nails and moisturizing hands.

17. A method of removing nail polish from nails comprising applying a composition comprising at least about 10% by weight of at least one polyhydric alcohol compound, at least 10% by weight of at least one C2-C5 alcohol, at least 15% by weight of at least one high boiling point ester compound, at least one thickening agent, and at least 5% by weight of at least one water-soluble abrasive having a hardness which provides mechanical exfoliation during said removing of nail polish from nails, wherein the composition comprises less than about 5% by weight of oil, all weights being based on the weight of the composition, to nails onto which nail polish has been previously applied and removing the nail polish from the nails.

18. The composition of claim 1, wherein the composition is essentially free of oil.

19. The composition of claim 1, wherein the composition is substantially free of oil.

20. The method of claim 17, wherein the composition comprises from 10% to 50% by weight of at least one polyhydric alcohol compound, from 10% to 50% by weight of at least one C2-C5 alcohol, from 15% to 50% by weight of at least one high boiling point ester compound, and from 5% to 20% by weight of at least one water-soluble abrasive, all weights being based on the weight of the composition.

* * * * *